US00PP22201P2

(12) United States Plant Patent

Herrera Valenzuela et al.

(10) Patent No.: US PP22,201 P2

(45) Date of Patent: Oct. 18, 2011

(54) *ALSTROEMERIA* PLANT NAMED 'JALEA'

(50) Latin Name: *Alstroemeria hybrida*
Varietal Denomination: Jalea

(75) Inventors: Camilo Herrera Valenzuela, Bogotá (CO); Henry Belalcázar Valencia, Bogotá (CO)

(73) Assignee: C.I. Valmar S.A., Bogotá (CO)

( * ) Notice: Subject to any disclaimer, the term of this patent is extended or adjusted under 35 U.S.C. 154(b) by 115 days.

(21) Appl. No.: 12/658,045

(22) Filed: Feb. 1, 2010

(51) Int. Cl.
*A01H 5/00* (2006.01)

(52) U.S. Cl. ..... Plt./309

(58) Field of Classification Search ..... Plt./309
See application file for complete search history.

(56) References Cited

U.S. PATENT DOCUMENTS

PP9,142 P * 5/1995 Amador ..... Plt./309
PP19,204 P2 * 9/2008 Jacobs ..... Plt./309

* cited by examiner

*Primary Examiner* — Wendy C Haas
(74) *Attorney, Agent, or Firm* — C. A. Whealy

(57) ABSTRACT

A new and distinct cultivar of *Alstroemeria* plant named 'Jalea', characterized by its erect and strong flowering stems; vigorous growth habit; purple and white-colored flowers arranged in symmetrical umbels; and excellent postproduction longevity.

1 Drawing Sheet

Botanical designation: *Alstroemeria hybrida.*
Cultivar denomination: 'JALEA'.

BACKGROUND OF THE INVENTION

The present invention relates to a new and distinct cultivar of *Alstroemeria* plant, botanically known as *Alstroemeria hybrida*, commercially used as a cut flower *Alstroemeria*, and hereinafter referred to by the name 'Jalea'.

The new *Alstroemeria* plant is a product of a planned breeding program in Madrid, Cundinamarca, Colombia. The objective of the breeding program was to create new *Alstroemeria* cultivars with attractive flower color and excellent postproduction longevity.

The new *Alstroemeria* plant originated from a cross-pollination conducted by the Inventors in Madrid, Cundinamarca, Colombia in April, 2001 of a proprietary selection of *Alstroemeria hybrida* identified as code number PJA 520, not patented, as the female, or seed, parent with a proprietary selection of *Alstroemeria hybrida* identified as code number JAH502, not patented, as the male, or seed, parent. The new *Alstroemeria* plant was discovered and selected by the Inventors as a single flowering plant from within the progeny of the stated cross-pollination grown in a controlled greenhouse environment in Madrid, Cundinamarca, Colombia in August, 2003.

Asexual reproduction of the new *Alstroemeria* plant by rhizome divisions in a controlled greenhouse environment in Madrid, Cundinamarca, Colombia since September, 2003, has shown that the unique features of this new *Alstroemeria* plant are stable and reproduced true to type in successive generations.

SUMMARY OF THE INVENTION

Plants of the new *Alstroemeria* have not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'Jalea'. These characteristics in combination distinguish 'Jalea' as a new and distinct cultivar of *Alstroemeria* plant:

1. Erect and strong flowering stems.
2. Vigorous growth habit.
3. Purple and white-colored flowers arranged in symmetrical umbels.
4. Excellent postproduction longevity.

Plants of the new *Alstroemeria* can be compared to plants of the parent selections. Plants of the new *Alstroemeria* differ from plants of the parent selections primarily in flower color as plants of the parent selections have violet and white-colored flowers.

Plants of the new *Alstroemeria* can be compared to plants of *Alstroemeria hybrida* 'Esperanza', not patented. In side-by-side comparisons conducted in Madrid, Cundinamarca, Colombia, plants of the new *Alstroemeria* differed primarily from plants of 'Esperanza' in the following characteristics:

1. Plants of the new *Alstroemeria* had larger umbels than plants of 'Esperanza'.
2. Plants of the new *Alstroemeria* had more flowers per inflorescence than plants of 'Esperanza'.
3. Plants of the new *Alstroemeria* and 'Esperanza' differed in flower color.
4. Plants of the new *Alstroemeria* had longer and thicker pedicels than plants of 'Esperanza'.

BRIEF DESCRIPTION OF THE PHOTOGRAPHS

The accompanying colored photographs illustrate the overall appearance of the new *Alstroemeria* plant, showing the colors as true as it is reasonably possible to obtain in colored reproductions of this type. Colors in the photographs may differ slightly from the color values cited in the detailed botanical description which accurately describe the colors of the new *Alstroemeria*.

The photograph at the bottom of the sheet comprises a side perspective view of a typical flowering stem of 'Jalea'.

The photograph at the top of the sheet is a close-up view of a typical inflorescence of 'Jalea'.

DETAILED BOTANICAL DESCRIPTION

The aforementioned photographs and following observations and measurements describe plants of the new *Alstroemeria* grown in Madrid, Cundinamarca, Colombia in a polyethylene-covered greenhouse in ground beds. During the production of the plants, day temperatures averaged 31.5° C., night temperatures averaged 6° C. and light levels averaged 21.4 KWH/m$^2$. Plants used for the photographs and description were four years old. Color references are made to The Royal Horticultural Society Colour Chart, 2007 Edition, except where general terms of ordinary dictionary significance are used.

Botanical classification: *Alstroemeria hybrida* 'Jalea'.

Parentage:

*Female, or seed, parent.*—Proprietary selection of *Alstroemeria hybrida* identified as code number PJA 520, not patented.

*Male, or pollen, parent.*—Proprietary selection of *Alstroemeria hybrida* identified as code number JAH502, not patented.

Propagation:

*Type.*—By rhizome divisions.

*Time to initiate roots.*—About two weeks at temperatures ranging from about 6° C. to 32° C.

*Time to produce a rooted young plant.*—About eight weeks at temperatures ranging from about 6° C. to 32° C.

*Root description.*—Fleshy, medium in thickness; close to 155A in color.

*Rooting habit.*—Freely branching; dense.

*Rhizomes.*—Shape: Rounded. Length: About 7 cm. Diameter: About 8.5 mm. Texture: Fleshy. Color: Close to NN155A.

Plant description:

*Plant and growth habit.*—Upright; freely branching, bushy appearance; vigorous growth habit.

*Time from planting to harvest of cut flowers.*—About 19 weeks.

*Flowering stem length.*—About 110 cm to 120 cm.

*Flowering stem diameter.*—About 18 cm.

Flowering stem description:

*Aspect.*—Erect.

*Length.*—About 110 cm to 120 cm.

*Diameter.*—About 6 mm.

*Internode length.*—About 3.5 cm to 6 cm.

*Strength.*—Strong.

*Texture.*—Smooth, glabrous.

*Color.*—Close to 146B.

Foliage description:

*Arrangement.*—Alternate, simple.

*Length.*—About 10.7 cm.

*Width.*—About 3 cm.

*Shape.*—Oblanceolate.

*Apex.*—Acute.

*Base.*—Attenuate.

*Margin.*—Entire.

*Texture, upper and lower surfaces.*—Smooth, glabrous; longitudinally ridged.

*Venation pattern.*—Parallel.

*Color.*—Developing leaves, upper surface: Close to 137B. Developing leaves, lower surface: Close to 137C. Fully expanded leaves, upper surface: Close to 137B; venation, close to 138A. Fully expanded leaves, lower surface: Close to 137C; venation, close to 138A.

*Petioles.*—Length: About 2.8 cm. Diameter: About 6 mm. Texture, upper and lower surfaces: Smooth, glabrous. Color, upper and lower surfaces: Close to 137C.

Flower description:

*Flower type and arrangement.*—Single cup-shaped flowers arranged in compound umbels; flowers face upright to outwardly; perianth segments separate.

*Flowering habit.*—Freely flowering with about 18 open flowers and flower buds per inflorescence.

*Natural flowering season.*—Flowering continuous year round in a greenhouse in Colombia; plants begin flowering about 19 weeks after planting.

*Fragrance.*—None detected.

*Flower longevity as a cut flower.*—About two weeks; flowers not persistent.

*Flower buds (showing color).*—Length: About 4.2 cm. Diameter: About 1.5 cm. Shape: Oblanceolate to obovate. Color: Towards the apex, close to 146A to 146B; mid-section, close to 145B; towards the base, close to 145C tinted with close to 186C.

*Umbel height.*—About 15 cm.

*Umbel diameter.*—About 15 cm by 18 cm.

*Flower diameter.*—About 5.5 cm.

*Flower length (height).*—About 5 cm.

*Flower depth.*—About 6 cm.

*Perianth.*—Arrangement: Six arranged in two whorls, each whorl with two lateral and one median segments. Outer perianth, lateral segments: Length: About 5.2 cm. Width: About 3.3 cm. Shape: Obovate. Apex: Wishbone; mucronate. Base: Attenuate. Margin: Entire; towards the apex, slightly sinuate. Texture, upper and lower surfaces: Smooth, glabrous. Color, when opening, upper surface: Close to NN155B; towards the margins, close to 70A to 70B; central apices, close to 146B to 146C. Color, when opening, lower surface: Close to 70A to 70B; towards the base, close to 157C to 157D; central apices, close to 146A to 146C. Color, fully opened, upper surface: Close to N78C; towards the base, close to 195C; central apices, close to 146C; main color becomes closer to 83B to 83C with development. Color, fully opened, lower surface: Close to 77B to 77C; towards the base, close to 195D; central apices, close to 146A to 146C. Outer perianth, median segment: Length: About 4.9 cm. Width: About 3.3 cm. Shape: Obovate. Apex: Wishbone, mucronate. Base: Attenuate. Margin: Entire; towards the apex, slightly sinuate. Texture, upper and lower surfaces: Smooth, glabrous. Color, when opening, upper surface: Close to NN155B; towards the margins, close to 70A to 70B; central apices, close to 146B. Color, when opening, lower surface: Close to 70A to 70B; towards the base, close to 157C to 157D; central apices, close to 146A to 146C. Color, fully opened, upper surface: Close to N78C; towards the base, close to 195C; central apices, close to 146C;

main color becomes closer to 83B to 83C with development. Color, fully opened, lower surface: Close to 77B to 77C; towards the base, close to 195D; central apices, close to 146A to 146C. Inner perianth, lateral segments: Length: About 5.6 cm. Width: About 2 cm. Shape: Oblanceolate. Apex: Cuspidate. Base: Attenuate. Margin: Entire; towards the apex, slightly serrate. Texture, upper and lower surfaces: Smooth, glabrous. Color, when opening, upper surface: Close to NN155A to NN155B; towards the apex, close to 194B and blushed with close to 77B to 77C; margins, blushed with close to 77B to 77C; random flecks, close to 183A. Color, when opening, lower surface: Close to NN155C tinted with close to 194C; mid-section and towards the margins, close to 77C. Color, fully opened, upper surface: Close to 157D; at the apex, close to 194B; margins, close to 77B to 77C; random flecks, close to 183B; main color becoming closer to N81A to N81C with development. Color, fully opened, lower surface: Close to 157C to 157D; margins, close to 77B to 77C; prominent mid-vein, close to 144A. Inner perianth, median segment: Length: About 4.5 cm. Width: About 2.1 cm. Shape: Oblanceolate. Apex: Cuspidate. Base: Attenuate. Margin: Entire; towards the apex, slightly serrate. Texture, upper and lower surfaces: Smooth, glabrous. Color, when opening, upper surface: Close to NN155A to NN155B; towards the apex, close to 194B and blushed with close to 77B to 77C; margins, blushed with close to 77B to 77C; random flecks, close to 183A. Color, when opening, lower surface: Close to NN155C tinted with close to 77C. Color, fully opened, upper surface: Close to 77B to 77C; towards the base, close to 157A; main color becoming closer to N81A to N81C with development. Color, fully opened, lower surface: Close to 77C to 77D; towards the base, close to 157A; prominent mid-vein, close to 144A.

*Pedicels.*—Length: About 8 cm. Diameter: About 2.5 mm. Strength: Strong. Angle: About 15° to 20° from the peduncle axis. Texture: Smooth, glabrous. Color: Close to 146B.

*Reproductive organs.*—Stamens: Quantity per flower: Six. Anther shape: Elongated. Anther length: About 7 mm. Anther diameter: About 3 mm. Anther color: Close to 197B. Pollen amount: Moderate. Pollen color: Close to N189B. Pistils: Quantity per flower: One. Pistil length: About 5.3 cm. Style length: About 4 cm. Style color: Close to 76B to 76C. Stigma shape: Three-parted. Stigma color: Close to N77C. Ovary color: Close to 146B tinted with close to 187B to 187C.

*Fruit/seed.*—Fruit and seed development has not been observed.

Disease/pest resistance: Plants of the new *Alstroemeria* have not been observed to be resistant to pathogens and pests common to *Alstroemeria*.

It is claimed:

1. A new and distinct *Alstroemeria* plant named 'Jalea' as illustrated and described.

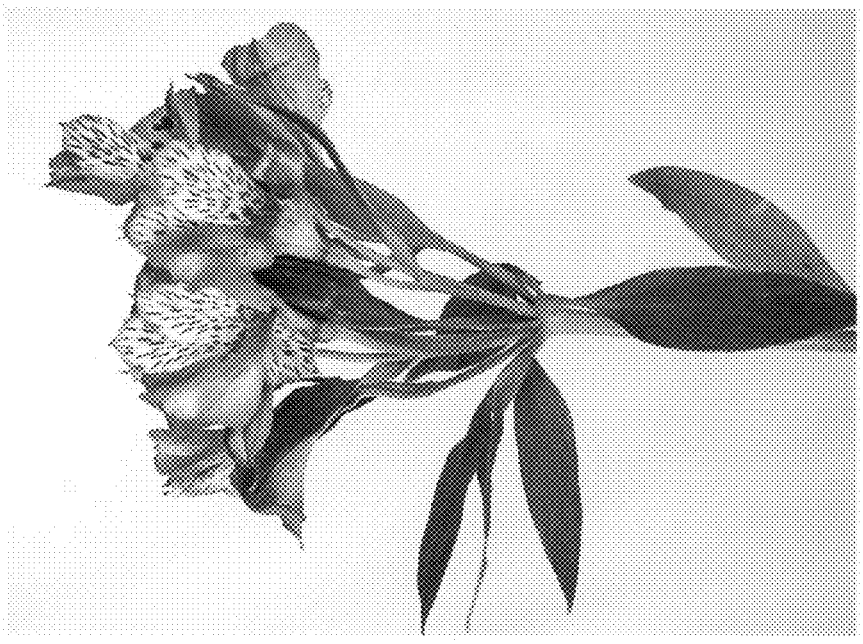
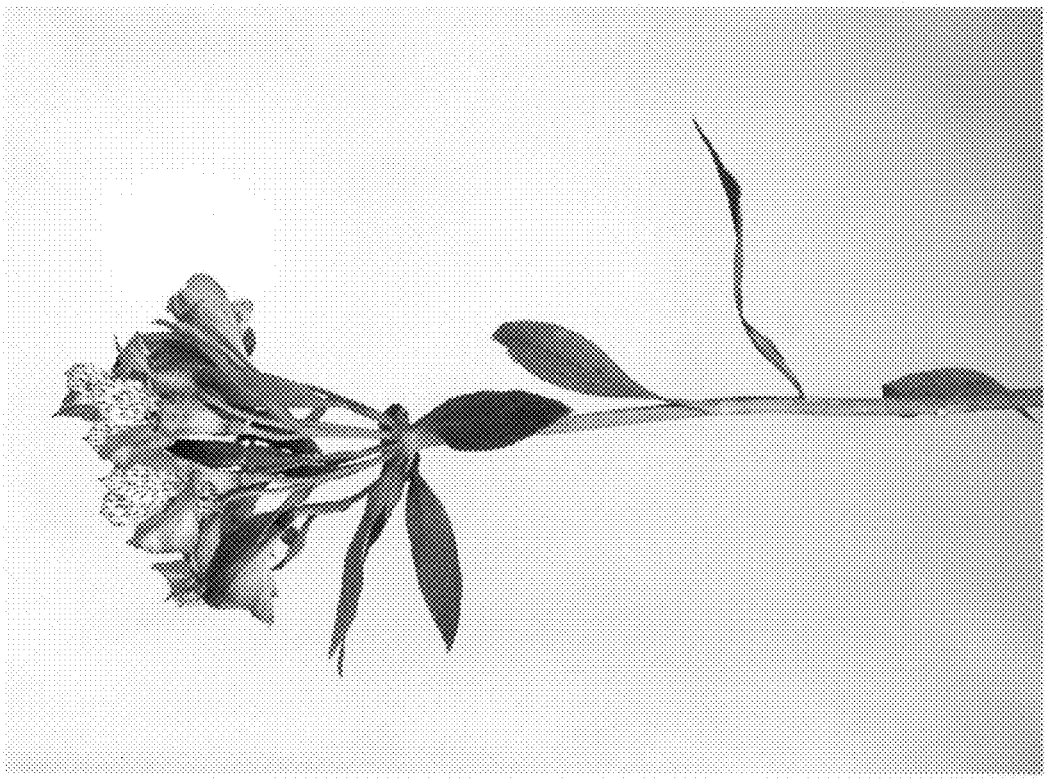

* * * * *